United States Patent
Javeri et al.

(10) Patent No.: US 9,655,846 B2
(45) Date of Patent: May 23, 2017

(54) METHODS FOR THE PREPARATION OF LIPOSOMES COMPRISING DRUGS

(71) Applicant: Indu Javeri, North Andover, MA (US)

(72) Inventors: Indu Javeri, North Andover, MA (US); Kaliappanadar Nellaiappan, Lexington, MA (US)

(73) Assignee: Indu Javeri, Andover, MA (US)

( * ) Notice: Subject to any disclaimer, the term of this patent is extended or adjusted under 35 U.S.C. 154(b) by 680 days.

(21) Appl. No.: 14/088,657

(22) Filed: Nov. 25, 2013

(65) Prior Publication Data

US 2014/0086983 A1 Mar. 27, 2014

Related U.S. Application Data

(63) Continuation of application No. 12/889,305, filed on Sep. 23, 2010, now Pat. No. 8,591,942.

(60) Provisional application No. 61/245,185, filed on Sep. 23, 2009.

(51) Int. Cl.
| | |
|---|---|
| *A61K 9/127* | (2006.01) |
| *A61K 9/19* | (2006.01) |
| *A61K 31/337* | (2006.01) |
| *A61K 9/00* | (2006.01) |

(52) U.S. Cl.
CPC ............ *A61K 9/127* (2013.01); *A61K 9/1278* (2013.01); *A61K 31/337* (2013.01); *A61K 9/0095* (2013.01); *A61K 9/19* (2013.01)

(58) Field of Classification Search
CPC ........................................................ A61K 9/127
USPC ........................................................ 424/450
See application file for complete search history.

(56) References Cited

U.S. PATENT DOCUMENTS

| | | | |
|---|---|---|---|
| 3,581,088 A | 5/1971 | Engels | |
| 4,291,024 A | 9/1981 | Turcotte | |
| 4,356,167 A * | 10/1982 | Kelly | A61K 9/1272 424/450 |
| 4,508,703 A | 4/1985 | Redziniak et al. | |
| 4,814,270 A | 3/1989 | Piran | |
| 4,857,319 A | 8/1989 | Crowe et al. | |
| 4,880,635 A * | 11/1989 | Janoff | A61K 9/1271 424/450 |
| 4,895,452 A * | 1/1990 | Yiournas | B01F 5/0057 264/4.1 |
| 4,911,928 A | 3/1990 | Wallach | |
| 4,970,076 A | 11/1990 | Horrobin | |
| 5,204,112 A | 4/1993 | Hope et al. | |
| 5,227,170 A | 7/1993 | Sullivan | |
| 5,230,899 A * | 7/1993 | Park | A61K 9/1277 264/4.1 |
| 5,316,771 A | 5/1994 | Barenholz et al. | |
| 5,415,869 A | 5/1995 | Straubinger et al. | |
| 5,580,575 A | 12/1996 | Unger et al. | |
| 5,589,189 A | 12/1996 | Moynihan | |
| 5,653,998 A | 8/1997 | Hamann et al. | |
| 5,660,855 A | 8/1997 | Male-Brune | |
| 5,676,928 A | 10/1997 | Klaveness et al. | |
| 5,684,169 A | 11/1997 | Hamada et al. | |
| 5,693,336 A | 12/1997 | Moynihan | |
| 5,747,060 A | 5/1998 | Sackler et al. | |
| 5,795,896 A | 8/1998 | Lofroth et al. | |
| 5,830,865 A | 11/1998 | Stjernfelt et al. | |
| 5,972,379 A | 10/1999 | Guo et al. | |
| 5,989,583 A | 11/1999 | Amselem | |
| 6,096,331 A | 8/2000 | Desai et al. | |
| 6,103,259 A * | 8/2000 | Roux | A61K 8/14 264/4.1 |
| 6,146,659 A | 11/2000 | Rahman | |
| 6,538,020 B2 | 3/2003 | Joshi-Hangal et al. | |
| 6,538,032 B1 | 3/2003 | Namgoong et al. | |
| 6,599,527 B1 | 7/2003 | Leigh et al. | |
| 7,217,770 B2 | 5/2007 | Seo et al. | |
| 7,811,602 B2 | 10/2010 | Cullis et al. | |
| 7,850,990 B2 | 12/2010 | Tardi et al. | |
| 2002/0039556 A1 | 4/2002 | Dyvik et al. | |
| 2002/0051813 A1 | 5/2002 | Boni et al. | |
| 2002/0094344 A1 | 7/2002 | Hope | |
| 2002/0103254 A1 | 8/2002 | Joshi-Hangal et al. | |
| 2002/0120015 A1 | 8/2002 | Dennis et al. | |
| 2003/0049302 A1 | 3/2003 | Pauletti et al. | |
| 2003/0113369 A1 | 6/2003 | Martin et al. | |
| 2003/0129222 A1 | 7/2003 | Lopez-Berestein et al. | |
| 2003/0138481 A1 | 7/2003 | Zadi | |
| 2004/0071775 A1 | 4/2004 | Jiang et al. | |

(Continued)

FOREIGN PATENT DOCUMENTS

| | | |
|---|---|---|
| DE | 1920765 A1 | 5/1970 |
| EP | 0173494 | 3/1986 |

(Continued)

OTHER PUBLICATIONS

Ahmad et al., Guggullipid derivatives: synthesis and applications, Chemistry and Physics of Lipids 163 (2010) 362-366.

Baedelmeijer et al., Entrapment by Cremophor EL decreases the absorption of paclitaxel from the gut, Cancer Chemother Pharmacol. Feb. 2002;49(2):119-25.

Barnadas-Rodriquez et al., Factors involved in the production of liposomes with a high-pressure homogenizer, Int J Pharm. Feb. 2001;213(1-2):175-86.

Dordunoo et al., International Journal of Pharmaceutics, Solubility and Stability of Taxol: Effects of Buffers and Cyclodextrins, (1996), 133:191-201.

European Journal of Hospital Pharmacists, Advances in Anticoagulant Care for the Prevention of Venous Thromboembolic Events After Othopaedic Surgery: A Pharmaceutical Perspective on Ximelagatran, a Novel Oral Direct Thrombin Inhibitor, 2004; Scientific Section (5):264-270.

(Continued)

*Primary Examiner* — Gollamudi Kishore
(74) *Attorney, Agent, or Firm* — Posternak Blankstein & Lund LLP

(57) ABSTRACT

Provided herein are methods for preparing liposomes comprising docetaxel and uses thereof. In certain embodiments, liposomes are prepared without using heat, organic solvents, proteins, and/or inorganic salts in the process. In certain embodiments, the liposomal preparations are used in the treatment of diseases or disorders.

33 Claims, 3 Drawing Sheets

(56) References Cited

U.S. PATENT DOCUMENTS

| | | |
|---|---|---|
| 2004/0126886 A1 | 7/2004 | Kan et al. |
| 2005/0123594 A1 | 6/2005 | Awasthi et al. |
| 2005/0142178 A1 | 6/2005 | Daftary et al. |
| 2006/0014699 A1 | 1/2006 | Edman et al. |
| 2006/0110441 A1 | 5/2006 | Wong et al. |
| 2006/0172003 A1 | 8/2006 | Meers et al. |
| 2006/0222696 A1* | 10/2006 | Okada ............... A61K 9/1271 424/450 |
| 2007/0292496 A1 | 12/2007 | Herrero Vanrell et al. |
| 2008/0102109 A1* | 5/2008 | Augustine ............ A61K 9/0019 424/450 |
| 2008/0274172 A1* | 11/2008 | Moscoso Del Prado ............... A61K 9/1277 424/450 |
| 2008/0286352 A1* | 11/2008 | Kumar ................ A61K 9/1272 424/450 |
| 2009/0017105 A1* | 1/2009 | Khattar ............... A61K 9/0019 424/450 |
| 2009/0041833 A1 | 2/2009 | Bettinger et al. |
| 2009/0074874 A1 | 3/2009 | Amano et al. |
| 2009/0162425 A1 | 6/2009 | Divi et al. |
| 2009/0169610 A1* | 7/2009 | Yamazaki ............ A61K 9/1271 424/450 |
| 2009/0191259 A1* | 7/2009 | Li ....................... A61K 9/1277 514/1.1 |
| 2009/0220587 A1 | 9/2009 | Allon et al. |
| 2009/0221953 A1 | 9/2009 | Kajimoto et al. |
| 2009/0291129 A1 | 11/2009 | Parmar |
| 2011/0177156 A1 | 7/2011 | Szoka, Jr. et al. |
| 2012/0107391 A1* | 5/2012 | Kelsey ............... A61K 31/4745 424/450 |

FOREIGN PATENT DOCUMENTS

| | | |
|---|---|---|
| EP | 0173494 A3 | 3/1986 |
| EP | 0249561 B1 | 12/1987 |
| EP | 0670166 A2 | 9/1995 |
| EP | 0923943 A1 | 6/1999 |
| EP | 1151755 A1 | 11/2001 |
| EP | 1547582 A1 | 6/2005 |
| JP | 3101614 A | 4/1994 |
| WO | 92/10166 | 6/1992 |
| WO | 95/12385 A1 | 5/1995 |
| WO | 97/20041 A1 | 6/1997 |
| WO | 97/30695 A1 | 8/1997 |
| WO | 99/04787 A1 | 2/1999 |
| WO | 99/13914 A1 | 3/1999 |
| WO | 99/45918 A1 | 9/1999 |
| WO | 99/49848 A1 | 10/1999 |
| WO | 00/00179 A1 | 1/2000 |
| WO | 00/03753 A2 | 1/2000 |
| WO | 00/40238 A1 | 7/2000 |
| WO | 00/71163 A1 | 11/2000 |
| WO | 01/01960 A1 | 1/2001 |
| WO | 01/05372 A2 | 1/2001 |
| WO | 01/30448 A1 | 5/2001 |
| WO | 01/87345 A1 | 11/2001 |
| WO | 02/07712 A2 | 1/2002 |
| WO | 02/43765 A2 | 6/2002 |
| WO | 02/080883 A2 | 10/2002 |
| WO | 03/033592 A1 | 4/2003 |
| WO | 03/045357 A1 | 6/2003 |
| WO | 2004/002468 A1 | 1/2004 |
| WO | 2004/047802 A2 | 6/2004 |
| WO | 2004/071466 A2 | 8/2004 |
| WO | 2005/000271 A1 | 1/2005 |

OTHER PUBLICATIONS

Gustafsson et al., The Direct Thrombin Inhibitor Melagatran and Its Oral Produg H 376/95: Intestinal Absorption Properties, Biochemical and Pharmacodynamic Effects, Thromb Res. Feb. 1, 2001;101(3):171-81.

Jahn et al., Unexpectedly High Entrapment Efficiencies in Nanometer Scale Liposomes With Hydrodynamic Focusing Using Continuous-Flow Microfluidics, Twelfth International Conference on Miniaturized Systems for Chemistry and Life Sciences, Oct. 12-16, 2008, San Diego, California, USA.

Nasongkla et al., Enhancement of solubility and bioavailability of beta-lapachone using cyclodextrin inclusions complexes, Pharm Res, Oct. 2003;20(10):1626-33.

O'Reilly et al., The effect of mixed micellar systems, bile salt/fatty acids, on the solubility and intestinal absorption of clofazimine (B663) in the anaestheised rat, International Journal of Pharmaceutics, 1994;109:147-154.

Pinnamaneni et al., Formulation approaches for orally administered poorly soluble drugs, Pharmazie. May 2002;57 (5):291-300.

Solomons, Organic Chemistry, 5th Edition, John Wiley & Sons, Inc., New York, 1992:1049-1052.

Szelag et al., The behaviour of modified monoacylglycerol emulsifiers in emulsion systems, Colloids and Surfaces A: Physicochemicals and Engineering Aspects, 1999;155:349-357.

Takada et al., Pharmaceutical Reasearch, Enhanced Selective Lymphatic Delivery of Cyclosporin A Solubilizers and Intensified Imunosuppresive Activity Against Mice Skin Allograft, (1986), 3(1):48-51.

Takahashi et al., Efficient preparation of liposomes encapsulating food materials using lecithins by a mechanochemical method, J Oleo Sci., 2007; 56(1):35-42.

Takahashi et al., Characterization and bioavailability of liposomes containing a ukon extract, Biosci Biotechnol Biochem., May 2008; 72(5):1199-205.

Thompson et al., Preparation of liposomes from milk fat globule membrane phospholipids using a microfluidizer, J Dairy Sci., Feb. 2006;89(2):410-9.

Trosko, in Mutation Research, 480-481, pp. 219-229, 2001.

Yousefi et al., Preparation and In Vitro Evaluation of a Pegylated Nano-Liposomal Formulation Containing Docetaxel, Sci Pharm. 2009;77:453-464.

Final Office Action dated Oct. 10, 2014 received in copending U.S. Appl. No. 12/889,248.

Madden et al., "Protection of large unilamellar vesicles by trehalose during dehydration: retention of vesicle contents," (1985) 817:67-74.

Office Action dated Apr. 16, 2014 received in copending U.S. Appl. No. 12/889,248.

Takahashi et al., "Liposomes encapsulating Aloe vera leaf gel extract significantly enhance proliferation and collagen synthesis in human skin cell lines," (2009) 58(12):643-650.

* cited by examiner

* The number represents mg/kg dose

* The number represents mg/kg dose

METHODS FOR THE PREPARATION OF LIPOSOMES COMPRISING DRUGS

CROSS REFERENCE TO RELATED APPLICATIONS

This application is a continuation of U.S. patent application Ser. No. 12/889,305 filed Sep. 23, 2010, which claims priority from U.S. Provisional Patent Application Ser. No. 61/245,185, filed Sep. 23, 2009, each of which is incorporated herein by reference in its entirety.

Provided herein are methods for preparing liposomes comprising docetaxel and uses thereof.

BACKGROUND

The bioavailability of a pharmaceutical drug depends largely in part on the solubility and stability of the drug. Many methods have been employed to improve bioavailability of a drug, including, but not limited to, pH adjustment, associating the drug in micelles of detergents, solubilization in an organic solvent, complexation with cyclodextrin or other polymers, and encapsulating the drug in a liposome bilayer (Strickley, R. G., *Pharmaceutical Research*, No. 21, 2004: 201-230). Either the drug itself or the excipients used to solubilize the drug may have side effects such as allergic reaction or hemolysis.

It is known that the solvents (e.g., ethanol, propylene glycol, polyethylene glycol, dimethylacetamide, dimethylsulfoxide ("DMSO")), complexing agents (for example, nicotinamide), and surfactants (for example, sodium oleate) are hemolytic and are therefore undesirable for use in injectable solutions. Other limitations to using organic solvents in injectable products include precipitation, pain, and inflammation upon injection.

Liposomes are microscopic lipid vesicles that are composed of a central aqueous cavity surrounded by a lipid membrane formed by concentric bilayer(s) (lamellas). Liposomes are able to incorporate hydrophilic substances (in the aqueous interior) or hydrophobic substances (in the lipid membrane). Liposomes can be unilamellar vesicles ("UMV"), having a single lipid bilayer, or multilamellar vesicles ("MLV"), having a series of lipid bilayers (also referred to as "oligolamellar vesicles"). The multilamellar vesicles typically range in size from 0.2 μm to 10 μm in diameter. See e.g., WO 98/006882. Although anti-hemolytic measures are commonly taken in formulations, maintaining a sufficient amount of liposome in formulation may not be feasible due to the incompatibility of the liposome with an excipient, or the instability of the liposome in the formulation. Further, reconstituting lyophilized formulations containing hydrophobic drugs is often difficult. This is the case, for example, in the reconstitution of docetaxel, sodium oleate, and liposomes. Moreover, liposomes are not stable in formulations containing concentrated organic solvents.

Unilamellar vesicles with a diameter of less than 0.2 μm (e.g. between 0.02 and 0.2 μm) are commonly known as small unilamellar vesicles ("SUV"). Unilamellar vesicles with a diameter greater than 0.45 μm (in some cases greater than 1 μm) are commonly known as large unilamellar vesicles ("LUV").

The bilayer(s) of liposomes most often comprise phospholipids, but may also comprise lipids including but not limited to fatty acids, fatty acid salts and/or fatty alcohols. The properties of the liposomes depend, among other factors, on the nature of the constituents. Consequently, if liposomes with certain characteristics are to be obtained, the charge of its polar group and/or the length and the degree of saturation of its fatty acid chains must be taken into account.

In addition, the properties of liposomes may be modified, e.g., to incorporate cholesterol and other lipids into the membrane, change the number of lipidic bilayers, or covalently join natural molecules (e.g., proteins, polysaccharides, glycolipids, antibodies, enzymes) or synthetic molecules (e.g., polyethyl glycol) to the surface. There are numerous combinations of phospholipids, optionally with other lipids or cholesterol, in an aqueous medium to obtain liposomes. Depending on the method of preparation and the lipids used, it is possible to obtain vesicles of different sizes, structures, and properties.

Another important parameter to consider with respect to the formation of liposomes is the rigidity of the lipidic bilayer. The hydrated lipid that forms part of the bilayer may be in either a liquid-crystalline (fluid) or gel state. As the temperature increases, the gel state is converted into the liquid-crystalline state. This occurs at a temperature known as the transition temperature (Tc), which is specific to each lipid. The Tc is directly proportional to chain length and inversely proportional to the degree of unsaturation of the fatty acids and depends on the nature of the polar group.

Despite this, common methods in the preparation of lipid vesicles, such as liposomes, comprise evaporating an organic solvent in which the lipids are dissolved and then dispersed in an optionally buffered aqueous solution. One exemplary method, known as the Rangham method, was originally described in Bangham et al., *J. Mol. Biol.*, 11:238-252 (1965). Variations of the Bangham method are known by those skilled in the art, some of which are described below.

Hydration of a Thin Lipidic Layer.

Starting with the organic solution of the constituent lipids of the bilayer, a lipidic film is prepared through removal of organic solvent, which can be achieved by means of evaporation (e.g., at reduced pressure in a rotary evaporator) or by lyophilization. The dry lipidic film obtained is hydrated by adding an aqueous solution and agitating the mixture at temperatures above the Tc.

Reverse-Phase Evaporation.

Starting with the organic solution of the constituent lipids of the bilayer, a lipidic film is prepared through removal of the organic solvent. The system is purged with nitrogen and the lipids are re-dissolved in a second organic solution, usually constituted by diethyl ether and/or isopropyl ether. The aqueous phase is added to the re-dissolved lipids. The system is maintained under continuous nitrogen. A gel is formed by removing the second organic solvent.

Solvent Injection.

The lipids, dissolved in an organic solvent, are injected slowly into an aqueous solution. The organic solvent used is often a water-miscible solvent, and the aqueous solution may be warmed.

Additional methods for the preparation of multilamellar vesicles can be found, e.g., in Szoka and Papandjopoulos, *Ann. Rev. Biophys. Bioeng.*, 2: 467-508 (1980), and Dousset and Douste-Blazy, Les Liposomes, Puisieux and Delattre, Editors, Tecniques et Documentation Lavoisier, Paris, pp. 1-73 (1985).

Further, when the incorporation of more than one lipid is desired, the lipids should remain homogeneously distributed in the liposomal vesicles. Traditionally, this is achieved by previously dissolving the lipids in an organic solvent and using the resulting organic solvent for preparing the liposomes.

U.S. Pat. No. 4,508,703 describes a method for obtaining powdery mixtures of at least one amphyphilic lipid and, optionally, at least one component of a hydrophobic or partially hydrophobic nature, a method which includes dissolving the components of the mixture in at least one organic solvent and atomizing the obtained solution into an inert gas. The method permits the preparation of lipidic mixtures which can be easily dispersed in an aqueous medium but does not avoid the use of organic solvents.

WO 92/10166 describes a method for preparing liposomes with an elevated encapsulation capacity. The method permits the use of mixtures of lipids; however, the mixture is obtained by means of previous dissolution of the lipids in an organic solvent and subsequent evaporation. In addition, the contact between the lipids and the aqueous solution of active agent is carried out at a temperature above the Tc.

Moreover, it is reported that, where liposomes are made without using organic solvents, other manipulations, which may result in formulations with certain unfavorable characteristics, are generally required. For example, U.S. Pat. App. Pub. No. 2008/0274172 describes methods of preparing liposomes containing at least two phospholipids without using organic solvents. However temperatures above the Tc were used to obtain stable liposomes from aqueous solutions containing inorganic salts.

Consequently, existing methods for preparing liposomes utilize organic solvents, protein, inorganic salts, and/or heat. Due to their toxicity and flammability, organic solvents are undesirable in the preparation of liposomes for pharmaceutical, cosmetic and other uses. Moreover, the use of organic solvents and proteins has negative repercussions in terms of production costs, safety, work hygiene and the environment. Similarly, the use of heat in the preparation of liposomes is undesirable in terms of production costs, safety, and the environment. The use of inorganic salts in the preparation of liposomes is undesirable as the introduction of inorganic salts increases the size of the liposome and/or results in a more turbid formulation. See e.g. Castile et al., *International Journal of Pharmaceutics*, 1999, vol. 188, issue 1, pp. 87-95. Thus, there is a need for a method for preparing liposomes without the use of undesirable agents and procedures.

SUMMARY

Provided herein are methods for preparing liposomes comprising docetaxel. In certain embodiments, liposomes are prepared without using heat, organic solvents, proteins, and/or inorganic salts in the process.

In one embodiment, a method is provided for the preparation of docetaxel containing liposomes, the method comprising:

(a) Combining one or more lipids in an aqueous medium at ambient temperature;
(b) Dispersing the lipids in the aqueous medium;
(c) Adding one or more sugars to the resulting mixture, thereby forming a solution of liposomes; and
(d) Adding docetaxel to the solution of liposomes.

In another embodiment, a method is provided for the preparation of docetaxel containing liposomes, the method comprising:

(a) Combining docetaxel and one or more lipids in an aqueous medium at ambient temperature;
(b) Dispersing the lipids in the aqueous medium; and
(c) Adding one or more sugars to the resulting mixture, thereby forming a solution of liposomes In certain embodiments, the liposomal preparation comprises one or more active agents in addition to docetaxel. In some embodiments, the one or more active agents are added during formation of the liposome. In other embodiments, the one or more active agents are added after the liposome or solution of liposomes has been prepared.

Also provided herein are uses of liposomal preparations comprising docetaxel in the treatment of diseases or disorders. In one embodiment, the liposomal preparation is suitable for parenteral administration to a patient suffering from said disease or disorder. In one embodiment, the patient is a human.

DEFINITIONS

As used herein, and unless otherwise specified, "lipid" is understood to be a fatty acid, fatty acid salt, fatty alcohol, or phospholipid. Lipids may also be read to include sterols, including, but not limited to, cholesterol; sphingolipids, including, but not limited to, sphingomyelin; glycosphingolipids including, but not limited to, gangliosides, globocides and cerebrosides; and surfactant amines including, but not limited to, stearyl, oleyl and linoleyl amines.

As used herein, and unless otherwise specified, "phospholipid" is understood to be an amphyphilic derivative of glycerol, in which one of its hydroxyl groups is esterified with phosphoric acid and the other two hydroxyl groups are esterified with long-chain fatty acids that can be equal to or different from each other and can be saturated or unsaturated. A neutral phospholipid is generally one in which the other phosphoric acid hydroxyl is esterified by an alcohol substituted by a polar group (usually hydroxyl or amino) and whose net charge is zero. A phospholipid with a charge is generally one in which the other phosphoric acid hydroxyl is esterified by an alcohol substituted by a polar group and whose net charge is positive or negative.

Examples of phospholipids include, but are not limited to phosphatidic acid ("PA"), phosphatidylcholine ("PC"), phosphatidylglycerol ("PG"), phophatidylethanolamine ("PE"), phophatidylinositol ("PI"), and phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoyl-phosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), distearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), diolcoylphosphatidylglycerol ("DOPG"), dipalmitoylphosphatidylglycerol ("DPPG"), distearoylphosphatidylglycerol ("DSPG"), 1-palmitoyl-2-oleoyl-phosphatidylglycerol ("POPG"), diarachidoylphosphatidylethanolamine ("DAPE"), didecanoyl-L-alpha-phosphatidylethanolamine ("DDPE"), dielaidoylphosphatidylethanolamine ("DEPE"), dilauroylphosphatidylethanolamine ("DLPE"), dilinoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), distearoylphosphatidylethanolamine ("DSPE"), 1-palmitoyl- 2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPI"), dilauroylphosphatidylinositol ("DLPI"), dilinoleoylphosphatidylinositol, dimyristoylphosphatidylinositol ("DMPI"), dioleoylphosphatidylinositol ("DOPI"), dipalmitoylphosphatidylinositol ("DPPI"), distearoylphosphatidylinositol ("DSPI"), 1-palmitoyl-2-oleoyl-phosphatidylinositol ("POPI"), diarachidoylphosphatidylserine ("DAPS"), didecanoyl-L-alpha-phosphatidylserine ("DDPS"), dielaidoylphosphatidylserine ("DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidylserine ("DPPS"), distearoylphosphatidylserine ("DSPS"), 1-palmitoyl-2-oleoyl-phosphatidylserine ("POPS"), diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, and 1-palmitoyl-2-oleoyl-sphingomyelin.

As used herein, and unless otherwise specified, "encapsulate" or "encapsulation" is understood to be the process of incorporating an active agent into liposomes or liposomal vesicles. The encapsulated active agent can remain in the aqueous interior or associate with membranes.

As used herein, and unless otherwise specified, the term "enhance" or "enhancing," when used in connection with the solubility of a compound, means that the methods provided herein result in the increased solubility of the compound as compared to the solubility of the same compound in water. Specifically, the term "enhance" or "enhancing" means that, when the methods provided herein are used, the solubility of a compound increases about 20 percent or more, about 40 percent or more, about 60 percent or more, about 80 percent or more, about 100 percent or more, or about 200 percent or more of the solubility of the same compound in a reference solvent. In some embodiments, the reference solvent is water.

As used herein, and unless otherwise specified, the term "hydrophobic compound" means a compound with little or no water solubility. In some embodiments, a hydrophobic compound has an intrinsic water solubility (i.e., water solubility of the unionized form) of less than about 20 percent by weight, about 15 percent by weight, about 10 percent by weight, about 5 percent by weight, about 1 percent by weight, about 0.1 percent by weight or about 0.01 percent by weight. In other embodiments, a hydrophobic compound has an intrinsic water solubility of less than about 10 mg/mL, about 7 mg/mL, about 5 mg/mL, about 3 mg/mL, about 1 mg/mL or about 0.1 mg/mL.

As used herein, or unless otherwise specified, the terms "aqueous medium" or "aqueous media" include any water based medium, e.g., water, saline solution, a sugar solution, a transfusion solution, a buffer, and any other readily available water-based medium. Further, an aqueous medium may contain one or more water soluble organic solvents. In the case of a parenteral solution, an aqueous medium is preferably sterile and suitable for use as a carrier of an active agent. Examples of aqueous media include, but are not limited to, water for injection, saline solution, Ringer's solution, D5W, or other solutions of water-miscible substances such as dextrose and other electrolytes.

As used herein, and unless otherwise specified, the term "fatty acid" means a compound whose structure is a carboxylic group attached to a hydrocarbon chain having one or more carbon atoms. The hydrocarbon chain may be saturated or unsaturated (i.e., alkyl, alkenyl or alkynyl hydrocarbon chains). Also, the hydrocarbon chain may be straight or branched. Moreover, in some embodiments, hydrogens in the hydrocarbon chain may be substituted.

As used herein, and unless otherwise specified, the term "fatty alcohol" means a compound whose structure is an alcohol group attached to a hydrocarbon chain having one or more carbon atoms. The hydrocarbon chain may be saturated or unsaturated (i.e., alkyl, alkenyl or alkynyl hydrocarbon chains). Also, the hydrocarbon chain may be straight or branched. Moreover, in some embodiments, hydrogens in the hydrocarbon chain may be substituted.

As used herein, and unless otherwise specified, the term "fatty acid salt" means a compound formed from a reaction between a fatty acid and an inorganic/organic base. In addition, the term encompasses a compound formed from a reaction between a fatty alcohol and an inorganic/organic acid. Examples of such acids include, but are not limited to, sulfuric and phosphoric acid. The hydrocarbon chain of the fatty acid salt may be saturated or unsaturated (i.e., alkyl, alkenyl or alkynyl hydrocarbon chains). In addition, the hydrocarbon chain may be straight or branched. Moreover, in some embodiments, hydrogens in the hydrocarbon chain may be substituted.

As used herein, and unless otherwise specified, the term "substituted" means a group substituted by one or more substituents including, but not limited to, alkyl, alkenyl, alkynyl, cycloalkyl, aroyl, halo, haloalkyl (e.g., trifluoromethyl), substituted or unsubstituted heterocycloalkyl, haloalkoxy (e.g., trifluoromethoxy), hydroxy, alkoxy, cycloalkyloxy, heterocylooxy, oxo, alkanoyl, aryl, substituted aryl, substituted or unsubstituted heteroaryl (e.g., indolyl, imidazolyl, furyl, thienyl, thiazolyl, pyrrolidyl, pyridyl, pyrimidyl and the like), arylalkyl, alkylaryl, heteroaryl, heteroarylalkyl, alkylheteroaryl, heterocyclo, aryloxy, alkanoyloxy, amino, alkylamino, arylamino, arylalkylamino, cycloalkylamino, heterocycloamino, mono- and di-substituted amino, alkanoylamino, aroylamino, aralkanoylamino, substituted alkanoylamino, substituted arylamino, substituted aralkanoylamino, carbamyl (e.g., $CONH_2$), substituted carbamyl (e.g., CONH-alkyl, CONH-aryl, CONH-arylalkyl or instances where there are two substituents on the nitrogen), carbonyl, alkoxycarbonyl, carboxy, cyano, ester, ether, guanidino, nitro, sulfonyl, alkylsulfonyl, arylsulfonyl, arylalkylsulfonyl, sulfonamido (e.g., $SO_2NH_2$), substituted sulfonamido, thiol, alkylthio, arylthio, arylalkylthio, cycloalkylthio, heterocyclothio, alkylthiono, arylthiono and arylalkylthiono.

As used herein, and unless otherwise specified, the term "alkyl" means a saturated straight chain or branched non-cyclic hydrocarbon having 1-20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methyl hexyl, 5-methylhexyl, 2,3-dimethyl butyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted. Unsaturated alkyl groups include alkenyl groups and alkynyl groups, which are discussed below.

As used herein, and unless otherwise specified, the term "alkenyl" means a straight chain or branched non-cyclic hydrocarbon having 2-20 carbon atoms, preferably 2-10 carbon atoms, most preferably 2-6 carbon atoms, and including at least one carbon-carbon double bond. Representative straight chain and branched ($C_2$-$C_{10}$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. The double bond of an alkenyl group can be unconjugated or conjugated to another unsaturated group. An alkenyl group can be unsubstituted or substituted.

As used herein, and unless otherwise specified, the term "alkynyl" means a straight chain or branched non-cyclic hydrocarbon having 2-20 carbon atoms, preferably 2-10 carbon atoms, most preferably 2-6 carbon atoms, and including at least one carbon-carbon triple bond. Representative straight chain and branched ($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. The triple bond of an alkynyl group can be unconjugated or conjugated to another unsaturated group. An alkynyl group can be unsubstituted or substituted.

As used herein, and unless otherwise specified, the term "pharmaceutically acceptable salt" refers to a salt prepared from pharmaceutically acceptable non-toxic acids or bases including inorganic acids and bases and organic acids and bases. Suitable pharmaceutically acceptable base addition salts for the compositions provided herein include, but are not limited to, metallic salts made from aluminum, calcium, lithium, magnesium, potassium, sodium, and zinc, or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see e.g., Remington's Pharmaceutical Sciences, 18$^{th}$ ed., Mack Publishing, Easton Pa. (1990) or Remington: The Science and Practice of Pharmacy, 19th ed., Mack Publishing, Easton Pa. (1995).

As used herein, the term "hydrate" means a compound provided herein, or a salt thereof, that further includes a stoichiometric or non-stoichiometric amount of water bound by non-covalent intermolecular forces.

As used herein, the term "clathrate" means a compound provided herein, or a salt thereof in the form of a crystal lattice that contains spaces (e.g., channels) that have a guest molecule (e.g., a solvent or water) trapped within.

As used herein, and unless otherwise indicated, the term "prodrug" means a derivative of a compound that can hydrolyze, oxidize, or otherwise react under biological conditions (in vitro or in vivo) to provide an active compound. Examples of prodrugs include, but are not limited to, derivatives and metabolites of a compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. Esterifying any of the carboxylic acid moieties present on the molecule conveniently forms the carboxylate esters. Prodrugs can typically be prepared using well-known methods, such as those described by Burger's Medicinal Chemistry and Drug Discovery 6th ed. (Donald J. Abraham ed., 2001, Wiley), and Design and Application of Prodrugs (H. Bundgaard ed., 1985, Harwood Academic Publishers Gmfh).

As used herein, and unless otherwise specified, the term "stable," when used in connection with a formulation, means that the active agent of the formulation, when prepared using the methods provided herein, remains solubilized for a specified amount of time and does not significantly degrade or aggregate or become otherwise modified (e.g., as determined by HPLC).

As used herein, and unless otherwise specified, "temperature below the Tc" is understood to be a temperature which is lower than the Tc of the lipid having the lowest Tc, and "temperature greater than the Tc" is understood to be a temperature which is greater than the Tc of the lipid having the highest Tc.

As used herein, and unless otherwise specified, the term "harmful ingredient," when used in connection with pharmaceutical compositions, means an ingredient commonly used in a pharmaceutical composition that may cause clinical side effects such as, but not limited to, hemolysis, hypersensitive reaction, peripheral neuropathies, and/or decrease in the bioavailability of the active ingredient of the composition. Examples of harmful ingredients include, but are not limited to: toxic solvents, including organic solvents such as ethanol, methanol, 1-propanol, 2-propanol, acetone, acetonitrile, ethyl acetate, methyl acetate, diethyl ether, dimethyl ether, diisopropyl ether, methyl tert-butyl ether ("MTBE"), tetrahydrofuran ("THF"), dichloromethane, chloroform, carbon tetrachloride, 1,2-dichloroethane, pentane, hexanes, heptane, petroleum ether, dioxane, ethylene glycol, diethylene glycol, diglyme, 1,2-dimethoxyethane, 1-butanol, 2-butanol, 2-butanone, benzene, toluene, dimethylsulfoxide ("DMSO"), dimethylformamide ("DMF"), hexamethylphosphoramide ("HMPA"), N-methylpyrrolidone, glycerin, nitromethane, triethyl amine, xylenes. CREMOPHOR® EL, and polyethylene glycol ("PEG"); co-detergents or surfactants such as polysorbates (e.g., Tweens) or vitamin E; oils such as Castor oil or corn oil; proteins such as HSA; or any other biologic which is potential source of contamination.

DETAILED DESCRIPTION

Figure 1:
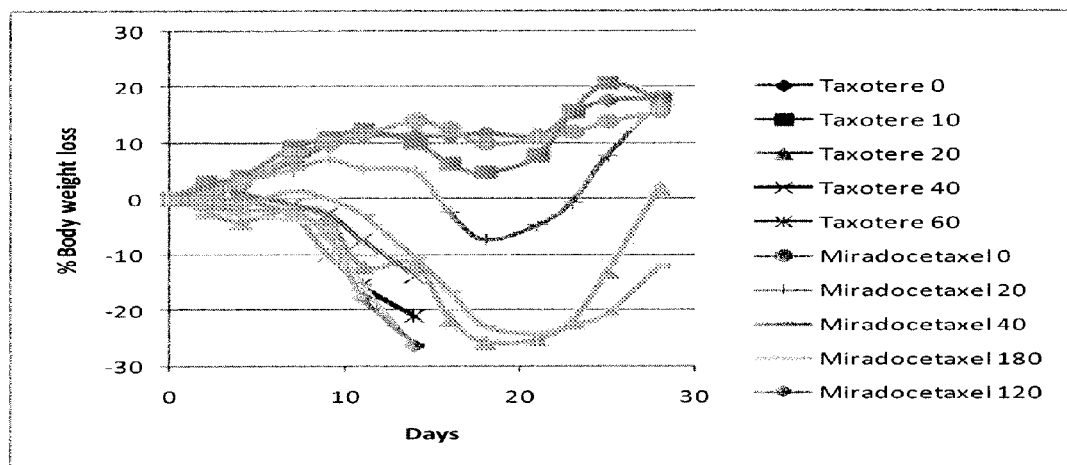
FIG. 1 depicts the percent body weight changes after injection of Taxotere® and Miradocetaxel™ (Q7DX3) to nude mice at different concentrations.

Provided herein is a method for the preparation of docetaxel containing liposomes, the method comprising:

(a) Combining one or more lipids in an aqueous medium at ambient temperature;

(b) Dispersing the lipids in the aqueous medium; and (c) Adding one or more sugars to the resulting mixture, thereby forming a solution of liposomes; and (d) Adding docetaxel to the solution of liposomes.

In another embodiment, a method is provided for the preparation of docetaxel containing liposomes, the method comprising:

(a) Combining docetaxel and one or more lipids in an aqueous medium at ambient temperature;

(b) Dispersing the lipids in the aqueous medium; and (c) Adding one or more sugars to the resulting mixture, thereby forming a solution of liposomes.

In another embodiment, at step (b), the method further comprises homogenization of the lipids in the aqueous medium.

In certain embodiments, the liposomal preparation comprises one or more active agents in addition to docetaxel. In some embodiments, the one or more active agents are added during formation of the liposome. In other embodiments, the one or more active agents are added after the liposome or solution of liposomes has been prepared.

In one embodiment, docetaxel is added as a solid. In another embodiment, docetaxel is added in an organic solvent. In another embodiment, docetaxel is added in organic solvent which further comprises one or more fatty acid salts, fatty acids and/or phospholipids.

In certain embodiments, the resulting liposomes are less than about 1 μm in diameter.

In one embodiment, the resulting liposomes are less than about 500 nm in diameter.

In one embodiment, the resulting liposomes are less than about 100 nm in diameter.

In one embodiment, at least one of the lipids is a phospholipid or a mixture of phospholipids. Examples of phospholipids include, but are not limited to, phosphatidic acid ("PA"), phosphatidylcholine ("PC"), phosphatidylglycerol ("PG"), phophatidylethanolamine ("PE"), phophatidylinositol ("PI"), and phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoylphosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), distearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), dioleoylphosphatidylglycerol ("DOPG"), dipalmitoylphosphatidylglycerol ("DPPG"), distearoylphosphatidylglycerol ("DSPG"), 1-palmitoyl-2-oleoyl-phosphatidylglycerol ("POPG"), diarachidoylphosphatidylethanolamine ("DAPE"), didecanoyl-L-alpha-phosphatidylethanolamine ("DDPE"), dielaidoylphosphatidylethanolamine ("DEPE"), dilauroylphosphatidylethanolamine ("DLPE"), di linoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), distearoylphosphatidylethanolamine ("DSPE"), 1-palmitoyl-2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPT"), dilauroylphosphatidylinositol ("DLPI"), dilinoleoylphosphatidylinositol, dimyristoylphosphatidylinositol ("DMPI"), dioleoylphosphatidylinositol ("DOPI"), dipalmitoylphosphatidylinositol ("DPPI"), distearoylphosphatidylinositol ("DSPI"), 1-palmitoyl-2-oleoyl-phosphatidylinositol ("POPI"), diarachidoylphosphatidylserine ("DAPS"), didecanoyl-L-alpha-phosphatidylserine ("DDPS"), dielaidoylphosphatidylserine ("DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidyl serine ("DPPS"), distearoylphosphatidylserine ("DSPS"), 1-palmitoyl-2-oleoyl-phosphatidylserine ("POPS"), diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, and 1-palmitoyl-2-oleoyl-sphingomyelin.

The phospholipids provided herein may be chiral or achiral. The chiral phospholipids provided herein may be D- or L-phospholipids, for example, L-α-phosphatidylcholine or L-3-phosphatidylcholine.

In one embodiment, L-α-phosphatidylcholine is used in the methods provided herein.

In another embodiment, provided herein is a method for the preparation of liposomes, the method comprising:

(a) combining sodium oleate and L-α-phosphatidylcholine in an aqueous medium at ambient temperature;

(b) dispersing sodium oleate and L-α-phosphatidylcholine in the aqueous medium; and (c) adding one or more sugars to the resulting mixture, thereby forming a solution of liposomes.

In another embodiment, the resulting solution contains 10% by weight trehalose.

In one embodiment, the docetaxel is a pharmaceutically acceptable salt, hydrate, clathrate or prodrug of docetaxel.

Examples of sugars that may be used in the methods provided herein include, but are not limited to, sucrose, glucose, fructose, lactose, maltose, mannose, galactose and trehalose.

In one embodiment, the sugar is trehalose.

In one embodiment, the liposomal preparation is suitable for parenteral administration to a patient suffering from one or more diseases or disorders.

In one embodiment, the patient is a human.

In one embodiment, the aqueous medium contains one or more additional active agents, or pharmaceutically acceptable salts, hydrates, clathrates or prodrugs thereof. Examples of active agents include, but are not limited to, lapachone (β-lapachone), taxanes (including, but not limited to, taxol, 7-epitaxol, 7-acetyl taxol, 10-desacetyltaxol, 10-desacetyl-7-epitaxol, 7-xylosyltaxol, 10-desacetyl-7-sylosyltaxol, 7-glutaryltaxol, 7-N,N-dimethylglycycltaxol, 7-L-alanyl-taxol, taxotere, and mixtures thereof), paclitaxel, colchicine, transferrin, cyclosporines, cyclosporin A, ketoprofen, propofol, acetylsalicylic acid, acetaminophen, amphotericin, digoxin, doxorubicin, daunorubicin, epirubicin, idarubicin, angiogenesis inhibitors (e.g, bevacizumab, ranibizumab, vitaxin, carboxyamidotriazole, combretastatin A-4, fumagillin analogs (e.g., TNP-470), CM101, IFN-α, interleukin-10, interleukin-12, platelet factor-4, suramin, SU5416, thrombospondin, VEGFR antagonists, angiostatin, endostatin, 2-methoxyestradiol, tecogalan, thalidomide, prolactin, linomide, angiopoietin-1, basic fibroblast growth factor, vascular endothelial growth factor), vinca-alkaloids (e.g., vinblastine, vincristine, vindesin, etoposide, etoposide phosphate, and teniposide), cytarabine, actinomycin, etoposide, bleomycin, gentamycin, cyclophosphamide, methotrexate, streptozotocin, cytosine, β-D-arabinofuranoside-5'-triphosphate, cytochrome C, cisplatin, N-phosphono-acetyl-L-aspartic acid, 5-fluoroorotic acid, acyclovir, zidovudine, interferons, aminoglycosides, cephalosporins, tetracyclines, propranolol, timolol, labetolol, clonidine, hydralazine, imipramine, amitriptyline, doxepim, phenyloin, diphenhydramine, chlorpheniramine, promethazine, prostaglandins, methotrexate, progesterone, testosterone, estradiol, estrogen, epirubicin, beclomethasone and esters, vitamin E, cortisone, dexamethasone and esters, betamethasone valerate, biphenyl dimethyl dicarboxylic acid, calcitonins, camptothecin, captopril, cephazoline, chloroquinine, chlorothiazole, co-agulation factors VIII and IX, d-alpha-tocopherol, dexamethasone, dichlofenac, etoposide, feldene, flubiprofen, 5-fluorouracil, fluoxetine, fusidic acid, gentamicin, glyburide, granisetron, growth hormones, indomethacin, insulin, itraconazole, ketoconazole, methotrexate, metronidazole, minoxidil, mitomycin, nafcillin, naproxen, ondansetron, oxyphenbutazone, parazosin, physostigmine, piroxicam, prednisolone, primaquine, quinine, ramipril, taxotane, tenoxicam, terazosin, triamcinolone, urokinase, opioid analgesics (e.g., alfentanil, anileridine, codiene, diamorphine, fentanyl, hydrocodone, hydromorphone, meperidine, morphine, oxycodone, oxymorphone, propoxyphene, sufentanil, pentazocine and nalbuphine), non-steroidal anti-inflammatory drugs (e.g., aspirin, indometacin, ibuprofen, mefenamic acid and phenylbutazone), angiotensin converting enzyme ("ACE") inhibitors (e.g., captoprilpolyene), protein kinase C inhibitors, antibiotics (e.g., imidazole and triazole antibiotics), folic acid, anthracycline antibiotics, anti-sense RNAs, tricathecums, microbial ribosomal-inactivating toxins (e.g., gelonin, abrin, ricin A chain, Pseudomonas exotoxin, diptheria toxin, pokeweed antiviral peptide), pipecolic acid derivatives (e.g., tacrolimus), plant alkaloids, dyes, radioisotope-labeled compounds, radiopaque compounds, radiosensitizers (e.g., 5-chloro-2'-deoxyuridine, 5-bromo-2'-deoxyuridine and 5-iodo-2'-deoxyuridine), fluorescent compounds, mydriatic compounds, bronchodilators, local anesthetics (e.g., dibucaine and chlorpromazine), antifungal agents (e.g., miconazole, terconazole, econazole, isoconazole, butaconazole, clotrimazole, itraconazole, nystatin, naftifine and amphotericin B), antiparasitic agents, hormones, hormone antagonists, immunomodulators, neurotransmitter antagonists, anti-diabetic agents, antiglaucoma agents, vitamins, narcotics, and imaging agents. For additional disclosure of active agents, see Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories. Rahway, N.J., 1999; Cecil Textbook of Medicine, 20th Ed., Bennett and Plum (eds.), W.B. Saunders, Philadelphia, 1996.

In one embodiment, the additional active agent is a hydrophobic compound, or a compound with poor solubility in water.

In another embodiment, the additional active agent is transferrin, or a pharmaceutically acceptable salt, hydrate, clathrate or prodrug thereof.

In another embodiment, the additional active agent is cyclosporine, or a pharmaceutically acceptable salt, hydrate, clathrate or prodrug thereof.

In one embodiment, the additional active agent is lapachone, or pharmaceutically acceptable salts, hydrates, clathrates or prodrugs thereof.

In one embodiment, the additional active agents are transferrin and lapachone, or pharmaceutically acceptable salts, hydrates, clathrates or prodrugs thereof.

As provided herein, the sequence of the addition of docetaxel results in enhanced solubility of the docetaxel. The conventional method of incorporating a hydrophobic drug into liposome is by adding the drug to lipid before liposome preparation. See, e.g., Immordino, M. L. et al., *Journal of Controlled Release*, 2003, 91: 417-429. By the conventional process, the incorporation of the drug is only 0.3 to 0.7 mg/mL. When docetaxel is added after liposome preparation, the incorporation of docetaxel is increased from 0.3 mg/mL to 5 mg/mL, which is more than 10 fold increase in solubility of the drug in lipid alone.

In the conventional liposome preparation, the drug to lipid molar percent ratio is 4-6% with the incorporation of drug into liposome efficiency is only 56%. See Immordino, M. L. et al., *Journal of Controlled Release*, 2003, 91: 417-429. Surprisingly, when docetaxel is added to pre-made lipsome, the drug to lipid molar ratio is 8% with an efficiency of incorporation of docetaxel into liposome of about 100%. Thus, as provided herein, the docetaxel load is increased at least about ten-fold, and the drug to lipid ratio is increased from 4-6% to 8% and incorporation efficiency is increased from 56% to 100%.

In certain embodiments, the efficiency of incorporation of docetaxel or other active agent into liposome is 50%, 60%, 70%, 80%, 90%, 95%, 98%, 99% or 100%. In certain embodiments, the efficiency of incorporation is 90%, 95%, 98%, 99% or 100%.

Without being limited to a particular theory or mechanism, the increase in incorporation of docetaxel to pre-made liposome (e.g., to a concentration of about 5 mg/mL) may be due to increase in surface area of liposome.

In another embodiment, provided herein is a docetaxel liposomal composition prepared by a method comprising:
 (a) Combining one or more lipids in an aqueous medium at ambient temperature;
 (b) Dispersing the lipids in the aqueous medium;
 (c) Adding one or more sugars to the resulting mixture, thereby forming a solution of liposomes; and
 (d) Adding docetaxel to the solution of liposomes.

In another embodiment, a method is provided for the preparation of docetaxel containing liposomes, the method comprising:
 (a) Combining docetaxel and one or more lipids in an aqueous medium at ambient temperature;
 (b) Dispersing the lipids in the aqueous medium; and
 (c) Adding one or more sugars to the resulting mixture, thereby forming a solution of liposomes.

In one embodiment, the docetaxel is added as a solid.

In one embodiment, the docetaxel is added in an organic solvent.

In one embodiment, the docetaxel in organic solvent further comprises one or more fatty acid salts, fatty acids and phospholipids.

In one embodiment, the solution of liposomes may be sterile filtered.

In one embodiment, the solution of liposomes is lyophilized to increase the shelf life.

In one embodiment, the lyophilized formulation is reconstituted in aqueous solution at desirable higher or lower concentrations.

In certain embodiments, the methods provided herein result in stable solutions, compositions or formulations comprising liposomes and docetaxel. In these embodiments, the docetaxel remains solubilized for a specified amount of time and does not significantly degrade, aggregate or become otherwise modified (e.g., as determined by HPLC). In some embodiments, the stable solutions comprise one or more additional active agents.

In some embodiments, about 70 percent or greater, about 80 percent or greater or about 90 percent or greater of the one or more active agents remains solubilized after a week after dilution with an acceptable diluent at an elevated temperature (e.g., about 35° C. or higher).

In other embodiments, about 70 percent or greater, about 80 percent or greater or about 90 percent or greater of the one or more active agents remains solubilized after a week after dilution with an acceptable diluent at room temperature.

In other embodiments, about 70 percent or greater, about 80 percent or greater or about 90 percent or greater of the one or more active agents remains solubilized after a week at a reduced temperature (e.g., about 10° C. or lower).

In certain embodiments, the methods provided herein result in enhanced solubility of docetaxel, as compared to the solubility of the same active agent in an aqueous medium. Specifically, when the methods provided herein are used, the solubility of the docetaxel increases about 20 percent or more, about 40 percent or more, about 60 percent or more, about 80 percent or more, about 100 percent or more, or about 200 percent or more of the solubility of the same docetaxel in a reference solvent. In some embodiments, the methods provided herein result in enhanced solubility of one or more additional active agents. In some embodiments, the reference solvent is water.

Also provided herein is a method of treating a disease or disorder using a liposomal composition provided herein. In some embodiments, the disease or disorder includes, but is not limited to, oncological disorders, proliferative disorders, central nervous system disorders, autoimmune disorders, and inflammatory diseases or disorders.

Proliferative disorders (e.g. cancer) that may be treated by the methods provided herein include, but are not limited to, neoplasms, tumors (malignant and benign) and metastases, or any disease or disorder characterized by uncontrolled cell growth. The cancer may be a primary or metastatic cancer. Specific examples of cancers that can be prevented, managed, treated or ameliorated in accordance with the methods of the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias (e.g., acute leukemia, acute lymphocytic leukemia), acute myelocytic leukemias (e.g., myeloblastic, promyelocytic, myelomonocytic, monocytic, erythroleukemia leukemias and myelodysplastic syndrome), chronic leukemias (e.g., chronic myelocytic (granulocytic) leukemia, chronic lymphocytic leukemia, hairy cell leukemia), polycythemia vera, lymphomas (e.g., Hodgkin's disease, non-Hodgkin's disease), multiple myelomas (e.g., smoldering multiple myeloma, nonsecretory myeloma, osteosclerotic myeloma, plasma cell leukemia, solitary plasmacytoma and extramedullary plasmacytoma), Waldenstrom's macroglobulinemia, monoclonal gammopathy of undetermined significance, benign monoclonal gammopathy, heavy chain disease, bone and connective tissue sarcomas (e.g., bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma), brain tumors (e.g., glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma), breast cancer (e.g., adenocarcinoma, lobular (small cell) carcinoma, intraductal carcinoma, medullary breast cancer, mucinous breast cancer, tubular breast cancer, papillary breast cancer, Paget's disease, and inflammatory breast cancer), adrenal cancer (e.g., pheochromocytom and adrenocortical carcinoma), thyroid cancer (e.g., papillary or follicular thyroid cancer, medullary thyroid cancer and anaplastic thyroid cancer), pancreatic cancer (e.g., insulinoma, gastrinoma, glucagonoma, vipoma, somatostatin-secreting tumor, and carcinoid or islet cell tumor), pituitary cancers (e.g., Cushing's disease, prolactin-secreting tumor, acromegaly, and diabetes insipius), eye cancers (e.g., ocular melanoma such as iris melanoma, choroidal melanoma, and cilliary body melanoma, and retinoblastoma), vaginal cancers (e.g., squamous cell carcinoma, adenocarcinoma, and melanoma), vulvar cancer (e.g., squamous cell carcinoma, melanoma, adenocarcinoma, basal cell carcinoma, sarcoma, and Paget's disease), cervical cancers (e.g., squamous cell carcinoma, and adenocarcinoma), uterine cancers (e.g., endometrial carcinoma and uterine sarcoma), ovarian cancers (e.g., ovarian epithelial carcinoma, borderline tumor, germ cell tumor, and stromal tumor), esophageal cancers (e.g., squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma), stomach cancers (e.g., adenocarcinoma, fungating (polypoid), ulcerating, superficial spreading, diffusely spreading, malignant lymphoma, liposarcoma, fibrosarcoma, and carcinosarcoma), colon cancers, rectal cancers, liver cancers (e.g., hepatocellular carcinoma and hepatoblastoma, gallbladder cancers such as adenocarcinoma), cholangiocarcinomas (e.g., pappillary, nodular, and diffuse), lung cancers (e.g., non-small cell lung cancer, squamous cell carcinoma (epidermoid carcinoma), adenocarcinoma, large-cell carcinoma and small-cell lung cancer), testicular cancers (e.g., germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma), penile cancers, oral cancers (e.g., squamous cell carcinoma), basal cancers, salivary gland cancers (e.g., adenocarcinoma, mucoepidermoid carcinoma, and adenoidcystic carcinoma), pharynx cancers (e.g., squamous cell cancer, and verrucous), skin cancers (e.g., basal cell carcinoma, squamous cell carcinoma and melanoma, superficial spreading melanoma, nodular melanoma, lentigo malignant melanoma, acral lentiginous melanoma), kidney cancers (e.g., renal cell cancer, adenocarcinoma, hypernephroma, fibrosarcoma, transitional cell cancer (renal pelvis and/or uterer)), Wilms' tumor, bladder cancers (e.g., transitional cell carcinoma, squamous cell cancer, adenocarcinoma, carcinosarcoma), myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas, follicular lymphomas, carcinomas with p53 mutations, hormone dependent tumors of the breast, prostate and ovary, precancerous lesions such as familial adenomatous polyposis, and myelodysplastic syndromes.

Other specific diseases and disorders that may be treated by the methods provided herein include, but are not limited to, the following: allergic disorders, inflammation, asthma, arthritis, encephalitis, rheumatoid arthritis, osteoarthritis, psoriatic arthritis, inflammatory osteolysis, chronic or acute obstructive pulmonary disease, chronic or acute pulmonary inflammatory disease, inflammatory bowel disease, Crohn's Disease, gout, Bechet's Disease, Henoch-Schonlein purpura ("HSP"), septic shock, sepsis, meningitis, colitis, inflammation due to reperfusion, psoriasis, fibrosis including pulmonary fibrosis, Parkinson's disease, bradykinesia, muscle rigidity, Parkinsonian tremor, Parkinsonian gait, motion freezing, depression; defective long-term memory, Rubinstein-Taybi syndrome (RTS), dementia, sleep disorders, insomnia, postural instability, hypokinetic disorders, hyperkinetic disorders, synuclein disorders, multiple system atrophies, striatonigral degeneration, olivopontocerebellar atrophy, Shy-Drager syndrome, motor neuron disease with parkinsonian features, Lewy body dementia, Tau pathology disorders, progressive supranculear palsy, corticobasal degeneration, frontotemporal dementia; amyloid pathology disorders, mild cognitive impairment, Alzheimer disease, Alzheimer disease with parkinsonism, Wilson disease, Hallervorden-Spatz disease, Chediak-Hagashi disease, SCA-3 spinocerebellar ataxia, X-linked dystonia parkinsonism, Huntington disease, prion disease, chorea, ballismus, dystonia tremors, Amyotrophic Lateral Sclerosis ("ALS"), CNS trauma, myoclonus, and diseases or disorders associated with undesired immune reaction (e g, organ rejection associated with an organ transplant).

EXAMPLES

Example 1

Preparation of Liposomes with No Drug: 6% L-α-Phosphatidylcholine (Soy) Liposome 6 g of L-α-phosphatidylcholine (Soy) was dispersed in 100 mL of water using a magnetic stirrer at 200 rpm for 10 minutes at ambient temperature. The dispersed liposome (multilayer) was passed through a Microfluidic homogenizer at 15,000 psi. Three cycles of passing resulted in a liposome less than 100 nm in diameter. Trehalose was then added to the liposome to a final concentration of 10% (w/w). The resulting stable isotonic liposome was either used as liquid or lyophilized.

Example 2

Preparation of Liposomes Encapsulated with Docetaxel 500 mg of docetaxel, 6 mg of sodium oleate, and 6 g of L-α-phosphatidylcholine (Soy) was dispersed in 100 mL of water using a magnetic stirrer at 200 rpm for 10 minutes at ambient temperature. The dispersed liposome (multilayer) was passed through a Microfluidic homogenizer at 15,000 psi. Three cycles of passing resulted in liposome encapsulated with 5 mg/mL docetaxel less than 100 nm in diameter. Trehalose was then added to liposome to a final concentration of 10% (w/w). The resulting stable isotonic liposome encapsulated with docetaxel was either used as liquid or lyophilized.

Example 3

Preparation of Liposomes Encapsulated with Docetaxel and Transferrin 500 mg of docetaxel, 200 mg of transferrin, 6 mg of sodium oleate, and of 6 g L-α-phosphatidylcholine (Soy) were dispersed in 100 mL of water using a magnetic stirrer at 200 rpm for 10 minutes at ambient temperature. The dispersed liposome (multilayer) was passed through a Microfluidic homogenizer at 15,000 psi. Three cycles of passing resulted in liposome encapsulated with 5 mg/mL docetaxel and 2 mg/ml transferrin less than 100 nm in diameter. Trehalose was then added to the liposome to a final concentration of 10% (w/w). The resulting stable isotonic liposome encapsulated with docetaxel and transferrin is either used as liquid or it could be lyophilized. This formulation specifically targets tumors, which requires angiogenesis for its survival. Tumors are known to have transferrin receptors; incorporating transferrin in docetaxel formulations will result in less toxicity and more efficacy, as the drugs are concentrated specifically in tumors without affecting the normal cells.

Example 4

Preparation of Liposomes Encapsulated with Docetaxel and Lapachone 500 mg of docetaxel, 200 mg of lapachone, 6 mg of sodium oleate and 6 g L-α-phosphatidylcholine (Soy) were dispersed in 100 mL of water using a magnetic stirrer at 200 rpm for 10 minutes at ambient temperature. The dispersed liposome (multilayer) was passed through a Microfluidic homogenizer at 15,000 psi. Three cycles of passing resulted in liposome encapsulated with 5 mg/mL docetaxel and 2 mg/mL lapachone less than 100 nm in diameter. Trehalose was then added to the liposome to a final concentration of 10% (w/w). The resulting stable isotonic liposome encapsulated with docetaxel and lapachone was either used as liquid or lyophilized. This formulation targets both nucleic acid (lapachone) and tubulin (docetaxel), thus increasing the efficacy of the treatment.

Example 5

Preparation of liposomes encapsulated with docetaxel, transferrin and lapachone 500 mg of docetaxel, 200 mg of transferrin, 200 mg of lapachone, 6 mg sodium oleate, and 6 g of L-α-phosphatidylcholine (Soy) were dispersed in 100 mL of water using a magnetic stirrer at 200 rpm for 10 minutes at ambient temperature. The dispersed liposome (multilayer) was passed through a Microfluidic homogenizer at 15,000 psi. Three cycles of passing resulted in liposome encapsulated with 5 mg/mL docetaxel, 2 mg/mL transferrin and 2 mg/mL lapachone less than 100 nm in diameter. Trehalose was then added to the liposome to a final concentration of 10% (w/w). The resulting stable isotonic liposome encapsulated with docetaxel, lapachone and transferrin was either used as liquid or lyophilized. This formulation specifically targets tumors, which require angiogenesis for their survival. Tumors are known to have transferrin receptors; incorporating transferrin in docetaxel formulations will result in less toxicity and more efficacy, as the drugs are concentrated specifically in tumors without affecting the normal cells. This formulation will further target both nucleic acid (lapachone) and tubulin (docetaxel), thus increasing the efficacy of the therapy as well.

Example 6

Solubilization of Docetaxel in Oleic Acid

Docetaxel (5 mg) was added to 31 µL of oleic acid and mixed using a VORTEX®. Ethanolamine (6 µL) was subsequently added and mixed using a VORTEX®. After mixing, the sample was dispersed in 963 µL of water for injection. Docetaxel was soluble and the formulation clear at 5 mg/mL. Docetaxel remained soluble, and the formulation was stable, upon dilution (1:10 in 2.5% glycerol) up to 24 hours as analyzed by a reverse phase high performance liquid chromatography method.

Example 7

Solubilization of Docetaxel in Sodium Oleate

Docetaxel (5.0 mg) was added to 1 mL of 0.05 M sodium oleate and mixed using a VORTEX®. Docetaxel was soluble and the formulation clear at 5.0 mg/mL. Docetaxel remained soluble, and the formulation was stable, upon dilution (1:10 in 2.5% glycerol) up to 24 hours as analyzed by a reverse phase high performance liquid chromatography method.

Example 8

Solubilization of Docetaxel in Sodium Caprylate

Docetaxel (2 mg) was added to 1 mL of 1 M sodium caprylate and mixed by a VORTEX®. Docetaxel was soluble and the formulation clear at 2 mg/mL. Docetaxel remained soluble, and the formulation was stable, upon dilution (1:2 2.5% glycerol) up to 24 hours as analyzed by a reverse phase high performance liquid chromatography method.

Example 9

Solubilization of Docetaxel in Sodium Linoleate

Docetaxel (7.0 mg) was added to 1 mL of 1 M sodium linoleate and mixed using a VORTEX®. Docetaxel was soluble and the formulation clear at 7.0 mg/mL. Docetaxel remained soluble, and the formulation was stable, upon dilution (1:10 2.5% glycerol) up to 24 hours as analyzed by a reverse phase high performance liquid chromatography method.

Example 10

Solubilization of Docetaxel in Oleate Liposome

Docetaxel (5 mg) was added to 1 mL of pre-made liposome containing 2 mM sodium oleate and 6% soy phosphatidyl choline, 10% trehalose, pH adjusted to 5-7 using Acetic acid, mixed using a VORTEX®, and microfluidized using a Microfluidizer with 10 passes at 15,000 psi. Five additional passes with the Microfluidizer at 15,000 psi were made to incorporate all 5 mg of the drug into 1 mL of pre-made liposome. Docetaxel was soluble and the formulation was transparent at 5 mg/mL. Docetaxel remained soluble, and the formulation was stable, upon dilution (1:10 in D5W) up to 48 hours as analyzed by a reverse phase high performance liquid chromatography method. The formulation is lyophilizable and the lyophilized formulation is stable for more than a year.

Example 11

Solubilization in Fatty Acid Dissolved in Organic Solvents

Hydrophobic or lipophilic compounds can be solubilized directly in sodium (or any ion) salt of fatty acid dissolved in an organic solvent. The organic solvent is subsequently removed using rotary evaporation, spray drying, or any other pharmaceutically acceptable processes. The drug-sodium salt of fatty acid mixture is subsequently dispersed in water, isotonic glycerol, or any pharmaceutically acceptable isotonic solution to achieve a desired concentration of the solubilized compound. For example, docetaxel (5 mg/mL) was dissolved in 100 mM sodium oleate in 100% ethanol. Ethanol was completely evaporated using rotary evaporation at 20° C. The docetaxel-sodium oleate was reconstituted with Water For Injection ("WFI") or 2.5% glycerol to provide 5 mg/mL, 10 mg/mL, or 20 mg/mL concentration of docetaxel. The reconstituted docetaxel remained in solution for 2 hours, 4 hours, 6 hours, 8 hours or 24 hours.

Example 12

Solubilization of Drug in Organic Solvent and Injection into Nanosome-Oleate

50 µl of Docetaxel in ethanol (100 mg/mL) was added to 1 mL of pre-made liposome containing 2 mM sodium oleate and 6% soy phosphatidyl choline, 10% trehalose and pH adjusted to 5-7 using Acetic acid, mixed using a VORTEX® and microfluidized using a Microfluidizer with 10 passes at 15,000 psi. Docetaxel was soluble and the formulation is transparent at 5 mg/mL. Docetaxel remained soluble, and the formulation was stable, upon dilution (1:10 in D5W) up to 48 hours as analyzed by a reverse phase high performance liquid chromatography method. The formulation is lyophilizable and the lyophilized formulation is stable for more than a year. The lyophilized product is reconstituted with water for injection at 5 mg, 10, or 20 mg/ml, concentration, essentially free of organic solvent.

Example 13

Safety of Miradocetaxel™ in Nanosome Formulation

Safety of docetaxel formulated as in Example 10 was studied using a nude mouse model to understand the maximum tolerable dose for Miradocetaxel™ as compared to Taxotere®. The maximum tolerated dose ("MTD"), defined as the highest dose of a drug or treatment that does not cause unacceptable side effects, is determined in clinical trials by testing increasing doses on different groups of people until the highest dose with acceptable side effects is found.

The MTD of Taxotere® and Miradocetaxel™ was addressed in nude mice. In the mice model, MTD is considered the highest dose which does not kill any mice in a group or does not cause 20% weight loss. The drugs were injected to group of 5 nude mice by I.V. at different concentrations. The injection schedules were Q7D3 (3 injections, one every 7 days). The percent weight loss and gross examination of internal organ were monitored for each animal.

Figure 2:
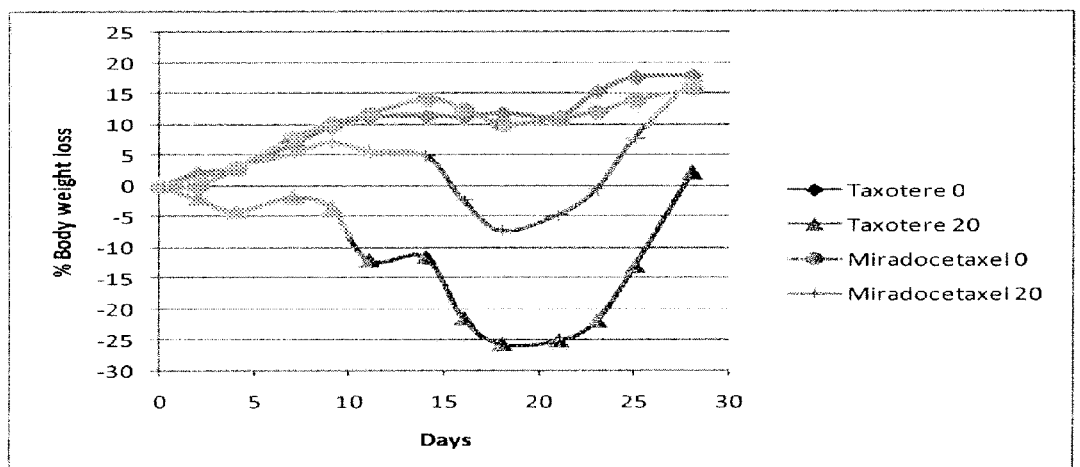
FIG. 2 depicts the percent body weight changes after injection of Taxotere® and Miradocetaxel™ (Q7DX3) to nude mice at 20 mg/kg dose.

The maximum tolerable doses in athymic nude mice for Taxotere® and Miradocetaxel™ are presented in Table 1 and percent body weight losses are presented in FIGS. 1 and 2.

TABLE 1

| Drug | MTD (mg/kg) |
| --- | --- |
| Miradocetaxel ™ | 30 |
| Taxotere ® | 15 |

The weight loss at 20 mg/mL concentration was more than 20% for the Taxotere® injection group, while less than 10% weight loss was noticed for the Miradocetaxel™ injection group (FIG. 2). The gross examination of organs suggested no damage in any group. Based on this MTD result Miradocetaxel™ is considered safer than Taxotere®.

Example 14

Figure 3:
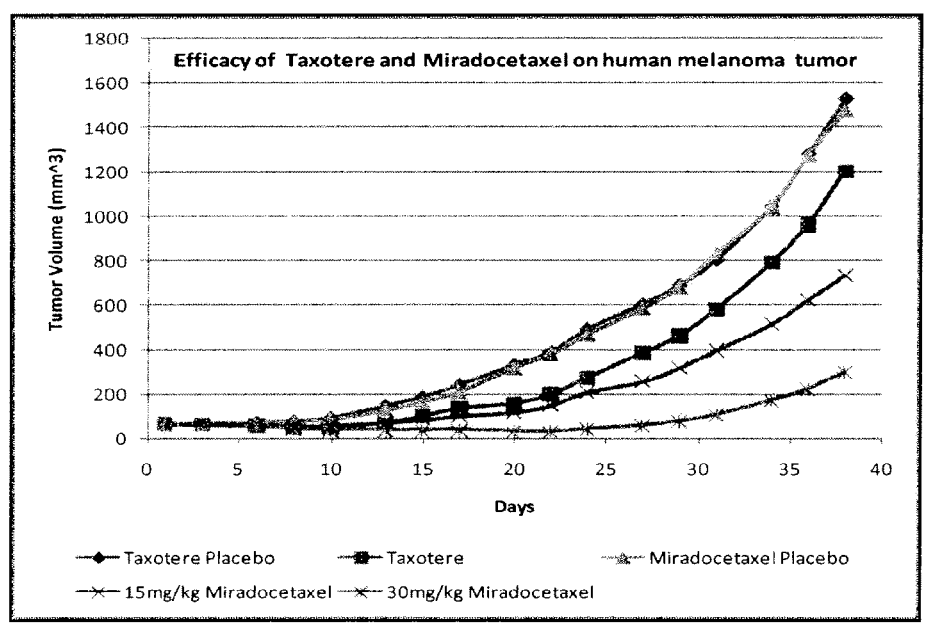
FIG. 3 depicts the efficacy of Taxotere® and Miradocetaxel™ on human melanoma tumors.
Figure 4:
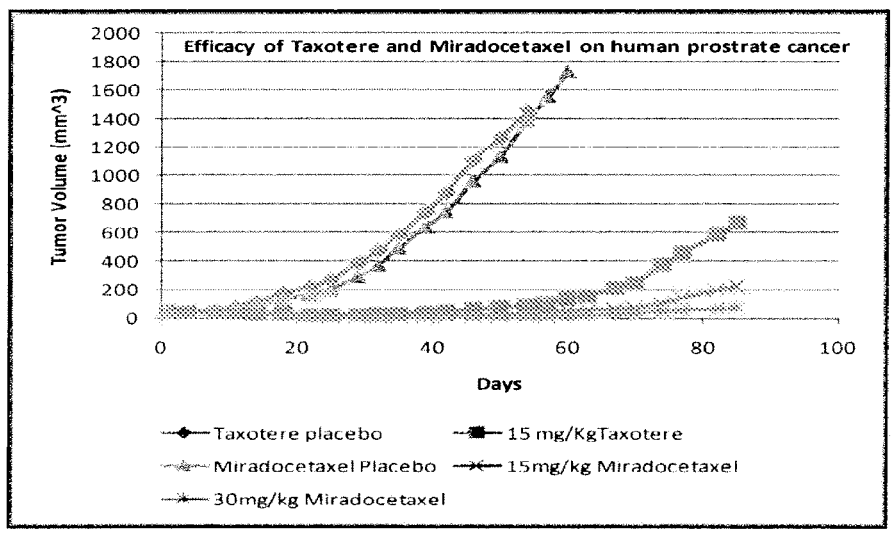
FIG. 4 depicts the efficacy of Taxotere® and Miradocetaxel™ on human prostate tumors.

Efficacy of Docetaxel Formulated in a Fatty Acid Salt Nanosome Using Xenograft of Human Melanoma Tumor and Prostate Tumor Efficacy of docetaxel formulated as in Example 12 was studied using the xenograft of human melanoma tumor and prostrate tumor. Two separate in-vivo studies were conducted each employing a different cancer cell line xenografted into mice. Athymic mice (nu/nu) implanted with either human melanoma tumor A375 or prostate tumor PC 3 cells and the cells were allowed to establish tumors. The mice were then treated with Taxotere® or Miradocetaxel™ (Q7DX3) (3 injections, one every 7 days). Taxotere® was delivered as a Tween 80-ethanol-saline formulation (15 mg/kg) and Miradocetaxel™ was delivered as sodium oleate-liposome formulation at concentrations of 15 mg/kg and 30 mg/kg. As shown in Example 13 above, Miradocetaxel™ delivery was shown to reduce toxicity as compared to Taxotere®. See FIGS. 1 and 2. This justified the use of the higher dose of 30 mg/kg for Miradocetaxel™. The administration of 15 mg/kg of Miradocetaxel™ was more efficacious than the administration of 15 mg/kg Taxotere®, as evidenced by tumor growth delay in both the tumor models. See FIGS. 3 and 4. Tumor growth inhibition (T/C) is the average tumor size of the treated groups (T) divided by the average tumor size of the control group (C) at a time when the average tumor size in the control group has reached approximately 1500 mm$^3$. A T/C value equal to or less than 42% is considered significant antitumor activity by the Drug Evaluation Branch of the Division of Cancer Treatment, National Cancer Institute (NCI). Tumor growth delay (T-C) is the difference between the average time, in days, required for the treatment group tumor (T) to reach approximately 250 mm$^3$, and the average time, in days, for the control group tumor (C) to reach the same size. The results obtained on T/C, T-C for are presented in Tables 2 and 3. The data indicates, that Taxotere® has no antitumor activity against melanoma, as T/C value was more than 42%. However, Miradocetaxel™ treatment has significant tumor inhibition with the T/C value of 20. Moreover, the tumor growth delay (T-C) results showed that Miradocetaxel™ treatment delays the growth of tumor to a greater degree than Taxotere®.

TABLE 2

A375 Human Melanoma Tumor Response to Treatments

| Group | Tumor Load (mm$^3$ day 38) | T/C (%) | 250 mm$^3$ (Day #) | T – C (Days) |
| --- | --- | --- | --- | --- |
| 13% Ethanol | 1527 | 100 | 18 | 0 |
| 15 mg/kg Taxotere ® | 1203 | 79 | 23 | 5 |
| Miradocetaxel ™*** placebo | 1473 | 96 | 18 | 0 |
| 15 mg/kg Miradocetaxel ™ | 732. | 48 | 27 | 9 |
| 30 mg/kg Miradocetaxel ™ | 299 | 20 | 37 | 19 |

*T/C: Tumor growth inhibition.
***All Miradocetaxel ™ formulations were reconstituted in water.

TABLE 3

PC 3 Human Prostate Tumor Response to Treatments

| Group | Tumor Load (mm$^3$ day 53) | T/C (%) | 250 mm$^3$ (Day #) | T – C (Days) |
| --- | --- | --- | --- | --- |
| 13% Ethanol | 1458 | 100 | 23 | 0 |
| 15 mg/kg Taxotere ® | 90.9 | 6.23 | 69 | 46 |
| Miradocetaxel ™*** placebo | 1387.6 | 100 | 26 | 0 |
| 15 mg/kg Miradocetaxel ™ | 34.5 | 2.48 | 86 | 60 |
| 30 mg/kg Miradocetaxel ™ | 11.35 | 0.82 | 98 | 72 |

*T/C: Tumor growth inhibition.
**T – C: Tumor growth delay. Time to achieve 250 mm$^3$ in the respective control group "C" was 23 and 26 days.
***All Miradocetaxel ™ formulations were reconstituted in water.

Example 15

Pharmacokinetic of Docetaxel Formulated in a Fatty Acid Salt Nanosome Using Rat Model System The pharmacokinetics of docetaxel in male rats following a single intravenous dosing of 25 mg/kg docetaxel in Taxotere® or Miradocetaxel™ formulation was evaluated. Taxotere® displayed a multi-exponential decay with harmonic mean $T_{1/2}$ values of ~4 to 5 hours. Miradocetaxel™ resulted in a 2.2-fold higher plasma docetaxel exposure (AUC(0-inf)) and ~2-fold lower systemic CL than the corresponding pharmacokinetics of docetaxel Taxotere® following dosing as shown in Table 4 and FIG. 5.

Figure 5:
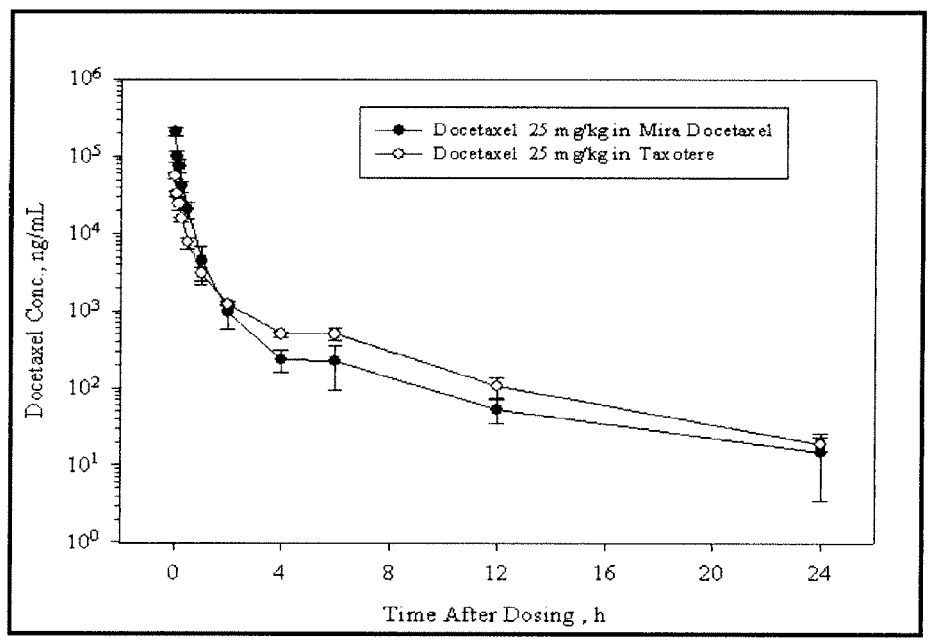
FIG. 5 depicts comparisons of docetaxel mean plasma concentrations in rats following a single 25 mg/kg dose of docetaxel in Taxotere® or Miradocetaxel™ formulations.

The plasma concentrations of docetaxel displayed the characteristics of a multi-exponential curve with harmonic mean $T_{1/2}$ of 4.02±0.266 hours (Table 4 and FIG. 5). Docetaxel in Taxotere® had AUC(0-inf), CL and $V_{ss}$ mean values were 21,100±1290 ng·h/mL, 1.19±0.0729 L/h/kg and 2.35±0.0503 L/kg, respectively (Table 4). Docetaxel in Miradocetaxel™, AUC(0-inf), CL and $V_{ss}$ mean values were 46,500±7640 ng·h/mL, 0.548±0.0953 L/h/kg and 0.408±0.176 L/kg, respectively (Table 4).

TABLE 4

Comparison of Docetaxel PK Parameters in Male Rats Following a Single 25 mg/kg Intravenous Dose of Docetaxel in Taxotere ® or Miradocetaxel ™

| Parameter | Taxotere | | Mira-Docetaxel | |
|---|---|---|---|---|
| | Mean | SD | Mean | SD |
| $T_{1/2}$, h[b] | 4.02 | 0.266 | 4.73 | 1.47 |
| AUC(0-inf), ng · h/mL | 21,100 | 1,250 | 46,500 | 7,640 |
| AUC(0-inf), µg · h/mL | 21.1 | 1.25 | 46.5 | 7.64 |
| $V_{ss}$, L/kg | 2.35 | 0.0503 | 0.408 | 0.176 |
| CL, L/h/kg | 1.19 | 0.0729 | 0.548 | 0.0953 |

[a] Docetaxel AUC(0-inf) following Miradocetaxel ™/docetaxel AUC(0-inf) following Taxotere ®
[b] Docetaxel CL following Miradocetaxel ™/docetaxel CL following Taxotere ®

Example 16

Unit Dosage Forms for Miradocetaxel™

Miradocetaxel™ is prepared as a lyophilized powder in vials of suitable size. A desired dosage can be filled in a suitable container and lyophilized to obtain a powder containing essentially fatty acid salt, phospholipid and docetaxel in the desired quantity. Such containers are then reconstituted with sterile aqueous diluent to the appropriate volume at the point of use to obtain a homogeneous clear solution of docetaxel in the diluent. This reconstituted solution can be directly administered to a patient either by injection or infusion with standard i.v. infusion sets.

All references cited herein are incorporated herein by reference in their entireties and for all purposes to the same extent as if each individual publication, patent or patent application was specifically and individually indicated to be incorporated by reference in its entirety for all purposes.

What is claimed is:

1. A suspension of liposomes in an aqueous medium, the liposomes encapsulating and solubilizing docetaxel at a concentration of at least about 5 mg docetaxel per ml of the aqueous medium.

2. The suspension of liposomes of claim 1 which is free of organic solvent.

3. The suspension of liposomes of claim 1 which is free of protein.

4. The suspension of liposomes of claim 1 which is free of surfactant.

5. The suspension of liposomes of claim 1 which is free of organic solvent, protein, and surfactant.

6. The suspension of liposomes of claim 1 which is isotonic.

7. The suspension of liposomes of claim 1 which is non-hemolytic.

8. The suspension of liposomes of claim 1 which is sterile.

9. The suspension of liposomes of claim 1 which is an injectable formulation.

10. The suspension of liposomes of claim 1, wherein the aqueous medium is adjusted to a pH of about 5-7.

11. The suspension of liposomes of claim 1, wherein the concentration of solubilized docetaxel is in the range from about 5 to about 20 mg/mL of the aqueous medium.

12. The suspension of liposomes of claim 1, wherein 90% or greater of the docetaxel remains solubilized after a week at a temperature of about 10° C. or lower.

13. The suspension of liposomes of claim 1, wherein 90% or greater of the docetaxel remains solubilized a week after dilution with a pharmaceutically acceptable diluent at room temperature.

14. The suspension of liposomes of claim 1, further comprising one or more active agents selected from the group consisting of lapachone, colchicine, transferrin, cyclosporin, and pharmaceutically acceptable salts thereof.

15. The suspension of liposomes of claim 1, wherein the suspension comprises a sugar.

16. The suspension of liposomes of claim 15, wherein the sugar is trehalose.

17. The suspension of liposomes of claim 16, wherein the trehalose is present at a concentration of about 10% by weight.

18. The suspension of liposomes of claim 1, wherein the liposomes are substantially unilamellar.

19. The suspension of liposomes of claim 1, wherein the liposomes have an average diameter of less than about 100 nm.

20. The suspension of liposomes of claim 1, wherein the liposomes comprise a phospholipid.

21. The suspension of liposomes of claim 20, wherein the phospholipid is soy phosphatidylcholine.

22. The suspension of liposomes of claim 1, wherein the liposomes comprise a fatty acid salt or fatty alcohol.

23. The suspension of liposomes of claim 1, wherein the liposomes comprise L-α-phosphatidylcholine and sodium oleate.

24. The suspension of liposomes of claim 1, wherein the suspension comprises 6 wt % soy phosphatidylcholine, 2 mM sodium oleate, 10 wt % trehalose, 5 mg/mL docetaxel.

25. The suspension of liposomes of claim 1, further comprising at least 2 mg lapachone per mL of the aqueous medium.

26. The suspension of liposomes of claim 1, further comprising at least 2 mg transferrin per mL of the aqueous medium.

27. The suspension of liposomes of claim 1, further comprising at least 2 mg lapachone and 2 mg transferrin per mL of the aqueous medium.

28. The suspension of liposomes of claim 1, wherein the molar ratio of liposomal lipid to encapsulated docetaxel is about 12.5 or less.

29. A lyophilized preparation of the suspension of liposomes of claim 1.

30. A lyophilized preparation of liposomes which upon reconstitution with water provides the suspension of liposomes of claim 1.

31. The lyophilized preparation of claim 30 which is stable for at least one year.

32. The lyophilized preparation of claim 30, wherein upon reconstitution with water the concentration of solubilized docetaxel is in the range from about 5 to about 20 mg/mL of the aqueous medium.

33. A suspension of liposomes in an aqueous medium, the liposomes encapsulating and solubilizing a hydrophobic compound at a molar ratio of about 12.5 moles or less of liposomal lipid per mole of hydrophobic compound, wherein the hydrophobic compound is selected from the group consisting of docetaxel, lapachone, and mixtures thereof.

* * * * *